United States Patent
Askarinya et al.

(10) Patent No.: US 9,252,415 B2
(45) Date of Patent: Feb. 2, 2016

(54) POWER SOURCES SUITABLE FOR USE IN IMPLANTABLE MEDICAL DEVICES AND CORRESPONDING FABRICATION METHODS

(75) Inventors: Mohsen Askarinya, Chandler, AZ (US); Andreas A. Fenner, Chandler, AZ (US); Erik J. Herrmann, Mesa, AZ (US); David A. Ruben, Mesa, AZ (US); John K. Day, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 902 days.

(21) Appl. No.: 13/524,304

(22) Filed: Jun. 15, 2012

(65) Prior Publication Data

US 2013/0337313 A1    Dec. 19, 2013

(51) Int. Cl.
*H01M 2/10* (2006.01)
*H01M 2/20* (2006.01)
(Continued)

(52) U.S. Cl.
CPC .............. *H01M 2/204* (2013.01); *A61N 1/378* (2013.01); *H01M 2/1066* (2013.01); *H01M 2/202* (2013.01); *H01M 2/22* (2013.01); *H01M 2/24* (2013.01); *H01M 2/266* (2013.01); *H01M 6/40* (2013.01); *H01M 6/46* (2013.01); *H01M 10/0436* (2013.01); *H01M 10/0525* (2013.01); *H01M 10/0562* (2013.01); *H01M 10/0585* (2013.01); *H01M 10/647* (2015.04);
(Continued)

(58) Field of Classification Search
CPC . H01M 2/204; H01M 2/1066; H01M 2/1011; H01M 2/202; H01M 2/22; H01M 2/24; H01M 2/266; H01M 10/0562; H01M 10/0585; H01M 10/647; H01M 6/40; H01M 6/46
See application file for complete search history.

(56) References Cited

U.S. PATENT DOCUMENTS 6,716,672 B2    4/2004    Val
7,877,874 B2    2/2011    Val
(Continued)

FOREIGN PATENT DOCUMENTS

WO    2010019485    2/2010

OTHER PUBLICATIONS

Wafer Level Stack—WDoD™—Reliable Miniaturization Technologies for Electronics located on the WorldWide Web at http://www.3d-plus.com/techno-wafer-level-stack-wdod.php.
(Continued)

*Primary Examiner* — Eugenia Wang
(74) *Attorney, Agent, or Firm* — Evans M. Mburu

(57) ABSTRACT

Arrays of planar solid state batteries are stacked in an aligned arrangement for subsequent separation into individual battery stacks. Prior to stacking, a redistribution layer (RDL) is formed over a surface of each wafer that contains an array; each RDL includes first and second groups of conductive traces, each of the first extending laterally from a corresponding positive battery contact, and each of the second extending laterally from a corresponding negative battery contact. Conductive vias, formed before or after stacking, ultimately couple together corresponding contacts of aligned batteries. If before, each via extends through a corresponding battery contact of each wafer and is coupled to a corresponding conductive layer that is included in another RDL formed over an opposite surface of each wafer. If after, each via extends through corresponding aligned conductive traces and, upon separation of individual battery stacks, becomes an exposed conductive channel of a corresponding battery stack.

4 Claims, 7 Drawing Sheets

(51) Int. Cl.
| | |
|---|---|
| *H01M 2/24* | (2006.01) |
| *H01M 2/26* | (2006.01) |
| *H01M 10/0562* | (2010.01) |
| *H01M 10/0585* | (2010.01) |
| *H01M 10/647* | (2014.01) |
| *H01M 6/40* | (2006.01) |
| *H01M 6/46* | (2006.01) |
| *H01M 2/22* | (2006.01) |
| *H01M 10/04* | (2006.01) |
| *H01M 10/0525* | (2010.01) |
| *A61N 1/378* | (2006.01) |
| *A61N 1/375* | (2006.01) |

(52) U.S. Cl.
CPC .............. *A61N1/3758* (2013.01); *Y02E 60/122* (2013.01); *Y10T 29/49112* (2015.01)

(56) References Cited

U.S. PATENT DOCUMENTS

| | | |
|---|---|---|
| 2002/0161404 A1 | 10/2002 | Schmidt |
| 2004/0258984 A1 | 12/2004 | Ariel et al. |
| 2006/0111752 A1 | 5/2006 | Greatbatch et al. |
| 2006/0129192 A1 | 6/2006 | Greatbatch et al. |
| 2009/0093772 A1 | 4/2009 | Genosar et al. |
| 2009/0102038 A1 | 4/2009 | Mcelrea et al. |
| 2009/0306594 A1 | 12/2009 | Pang et al. |
| 2010/0087778 A1 | 4/2010 | Genosar et al. |

OTHER PUBLICATIONS

Boone, "Planar Transformer Assemblies for Implantable Cardioverter Defibrillators", Filed Jun. 15, 2012, U.S. Appl. No. 13/524,222, 13 pages.

Boone, et al., "Wafer Level Packages of High Voltage Units for Implantable Medical Devices and Corresponding Fabrication Methods", Filed Jun. 15, 2012, U.S. Appl. No. 13/524,253, 29 pages.

Askarinya, et al., "Integrated Circuit Packaging for Implantable Medical Devices", Filed Jun. 15, 2012, U.S. Appl. No. 13/524,368, 21 pages.

POWER SOURCES SUITABLE FOR USE IN IMPLANTABLE MEDICAL DEVICES AND CORRESPONDING FABRICATION METHODS

FIELD OF THE DISCLOSURE

The present invention pertains to solid state battery power sources that may be employed in implantable medical devices, and, more specifically, to configurations and corresponding fabrication methods for planar solid state battery stacks.

BACKGROUND

FIG. 1 is a schematic showing a typical IMD 100, which is suitable for therapy delivery, implanted at a subcutaneous pectoral site in a patient 102. FIG. 1 illustrates IMD 100 including a hermetically sealed and biocompatible canister 104, for example, formed from a Titanium alloy, which houses a power source and electronic circuitry, and one or more electrical leads 106, which are coupled to the circuitry and extend distally from canister 104, through the venous system 110 and into the heart 108 of patient 102, for example, the right ventricle (RV). Those skilled in the art understand that the one or more leads 106 preferably include sensing and therapy delivery electrodes, which are coupled to the IMD circuitry via one or more lead connectors that terminate elongate insulated conductors of the electrodes, at a proximal end of lead(s) 106; the one or more lead connectors are plugged into a connector module 105, which is mounted on canister 104, to make electrical contact with the contained IMD circuitry via hermetically sealed feedthroughs.

FIG. 2 is a simplified circuit diagram of a portion of power source circuitry that may be employed by IMD 100. In particular FIG. 2 illustrates a plurality of batteries 22 in combination with switching circuitry 24, which may form one of a number of battery modules selectively connected in either a parallel or a series configuration and employed by the power source to store and discharge energy for pacing and/or defibrillation therapy, for example, through lead(s) 106 (FIG. 1). FIG. 2 further illustrates switching circuitry 24 including a solid state switch 241 and a switch driver unit 243 that receives trigger pulses, for example, from sensing circuitry (not shown), and, in response, provides a voltage output to cause switch 241 to conduct for discharge of the power source.

Each of batteries 22 may be a planar solid state type, for example, like a battery 32 shown in FIGS. 3A-B. United States Patent Application Publication No. 2006/0129192 and commonly assigned U.S. Pat. No. 6,782,290 describe, to different degrees, the general construction of exemplary planar solid state batteries and the arrangement of such batteries in modules or stacks, as a means to create a more compact/higher density power source in implantable medical devices. However, there is still a need for improved stack configurations and methods facilitating more efficient fabrication of relatively high density power sources from a plurality of solid state planar batteries.

SUMMARY

Methods of the present invention employ new combinations of state of the art fabrication techniques to more efficiently form embodiments of relatively high density power sources from a plurality of solid state planar batteries for use in implantable medical devices. According to some embodiments of the present invention, a power source includes a plurality of planar solid state batteries overlaying one another in an aligned arrangement and adhered to one another to form a stack, wherein conductive channels are exposed along opposite edges of the stack and extend along a height of the stack. The conductive channel that extends along a first edge of the stack is coupled to each positive battery contact in the stack by a corresponding conductive trace of a redistribution layer (RDL) of the corresponding battery in the stack; and the conductive channel that extends along a second edge of the stack is coupled to each negative battery contact in the stack by another conductive trace of each RDL. According to some alternate embodiments, a power source includes a plurality of planar solid state batteries overlaying one another in an aligned arrangement and adhered to one another to form a stack, wherein a conductive via extends through each positive battery contact of the stack and another conductive via extends through each negative battery contact of the stack. First and second conductive traces of a first RDL of each battery, formed over a first surface thereof, and corresponding first and second conductive bonding runners of a second RDL of each battery, formed over a second, opposing surface thereof, electrically connect the vias of aligned positive battery contacts together, and the vias of aligned negative battery contacts together, respectively.

According to methods of the present invention, that may be employed to fabricate the aforementioned embodiments, a plurality of wafers, each of which comprise an array of individual solid state batteries, are adhered together to form a stack, wherein the stack is configured such that the arrays of batteries overlay one another in an aligned arrangement, so that, in a subsequent step, individual battery stacks can be 'singulated', or separated from the stack of wafers. Prior to forming the stack of wafers, an RDL is formed over a first surface of each wafer, wherein each RDL includes a first conductive trace that is coupled to and extends laterally from each positive battery contact, into proximity with a first edge of the corresponding battery, and a second conductive trace that is coupled to and extends laterally from each negative battery contact, into proximity with a second, opposite edge of the corresponding battery. According to some methods, each wafer is formed as a reconstituted wafer by embedding a plurality of battery chips in a polymer mold compound to form the array of planar solid state batteries, and, after stacking the wafers, a plurality of conductive vias are formed through the stack so that each conductive via extends through a corresponding conductive trace of each corresponding aligned battery, to electrically couple corresponding electrical contacts of each aligned battery; and, when individual battery stacks are singulated, each conductive via becomes a conductive channel exposed along a corresponding edge of each individual battery stack. According to some alternative methods, when each wafer of the aforementioned plurality is an original silicon wafer in which the corresponding array of batteries is formed, the plurality of conductive vias is formed prior to forming the stack, such that each via extends through a corresponding battery contact; the vias of aligned batteries are electrically coupled together when the stack is formed, for example, by coupling each of the aforementioned conductive traces to a corresponding bonding runner of a second RDL, which is formed over a second, opposing surface of each wafer, after forming the vias and prior to forming the stack.

BRIEF DESCRIPTION OF THE DRAWINGS

The following drawings are illustrative of particular embodiments of the present invention and therefore do not limit the scope of the invention. The drawings are not to scale, and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
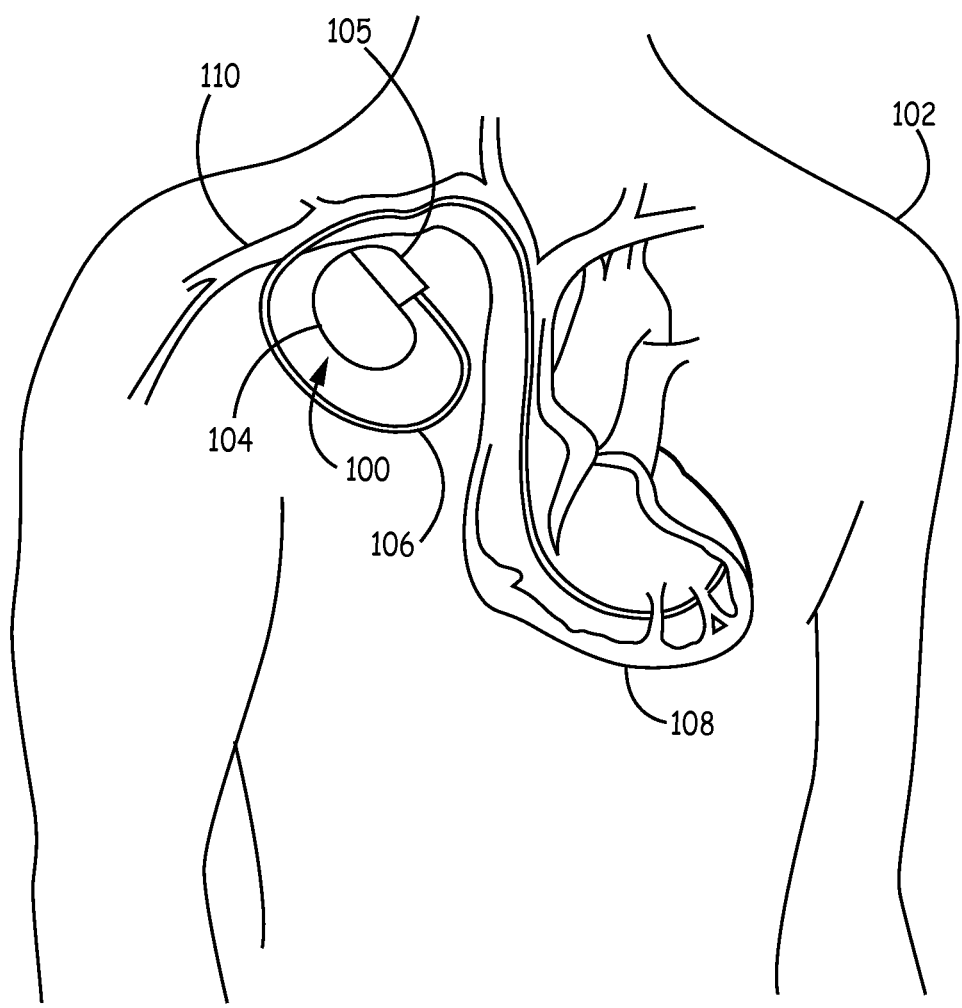
FIG. 1 is a schematic showing a typical placement of an implanted medical device.
Figure 2:
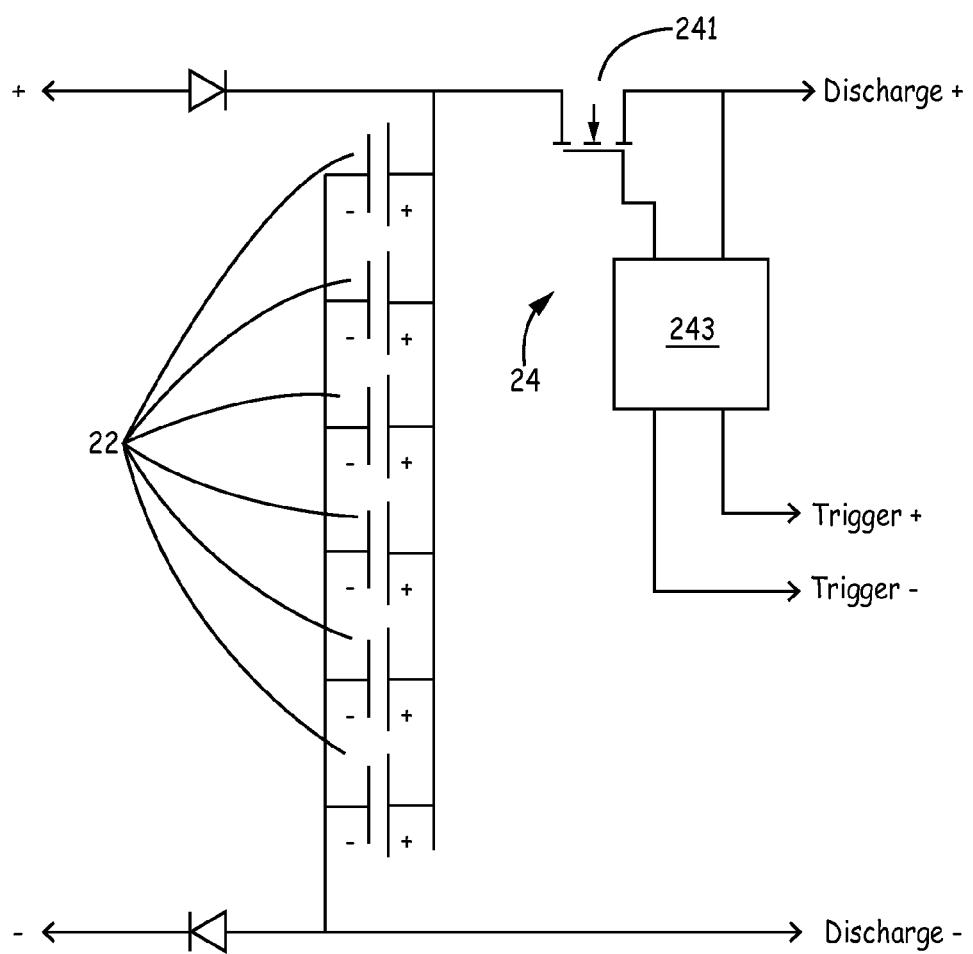
FIG. 2 is a simplified circuit diagram of a portion of circuitry that may be employed by the device shown in FIG. 1.
Figure 3B:
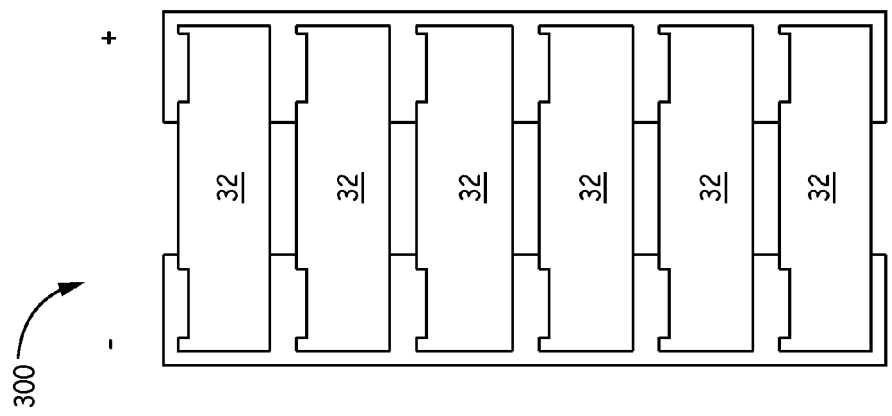
FIG. 3B is a perspective view of an exemplary stack of batteries.
Figure 3A:
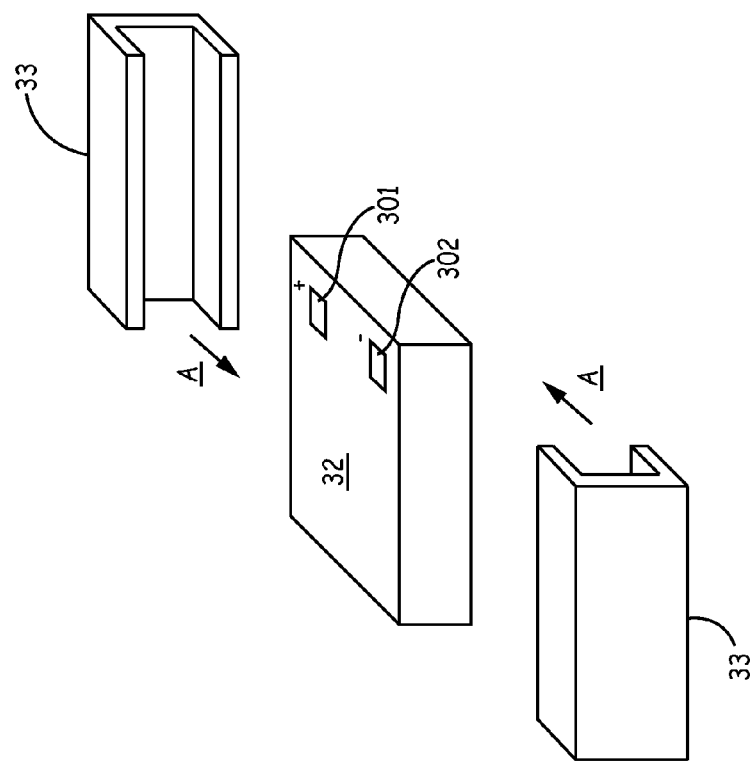
FIG. 3A is a perspective view of an exemplary planar solid state battery chip in conjunction with wrap-around leads positioned for assembly thereto.

FIG. 3A illustrates an exemplary planar solid state battery 32 having positive and negative contacts/terminals 301, 302 formed on a surface thereof, and a pair of wrap-around leads 33 positioned for attachment, per arrows A, to opposing edges of battery 32, such that each lead 33 is electrically coupled to a corresponding battery contact. Attached leads 33 facilitate assembly of a plurality of battery chips 32 together in a stack 300, for example, as shown in FIG. 3B, according to methods known to those skilled in the art, such that battery chips 32 are electrically coupled in parallel. Those skilled in the art will appreciate that each battery chip 32 may have been diced from a silicon wafer in which a relatively large number of batteries are originally fabricated, for example, using thin-film cell construction techniques known in the art, and employing lithium phosphorous oxynitride (LiPON) electrolyte material, wherein each battery chip 32 has a surface area of approximately 10-15 square centimeters and a thickness of approximately 14 micrometers.

Figure 4A:
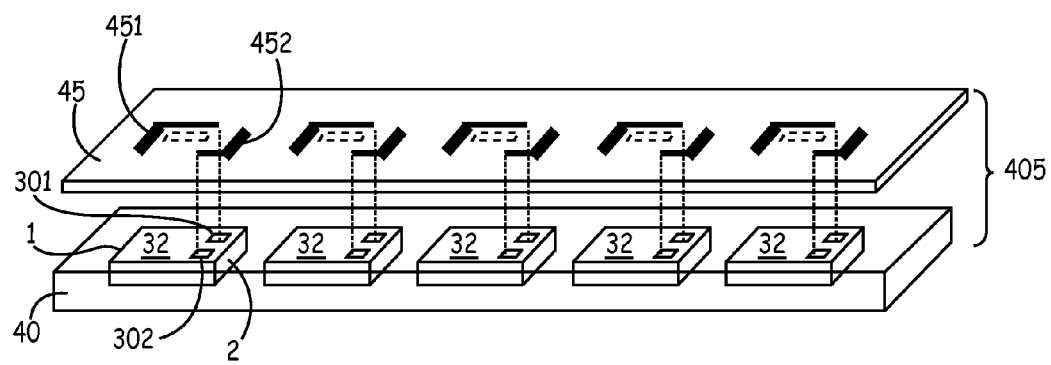
FIG. 4A is an exploded schematic of a single layer of a stack, fabricated according to some methods of the present invention.
Figure 4B:
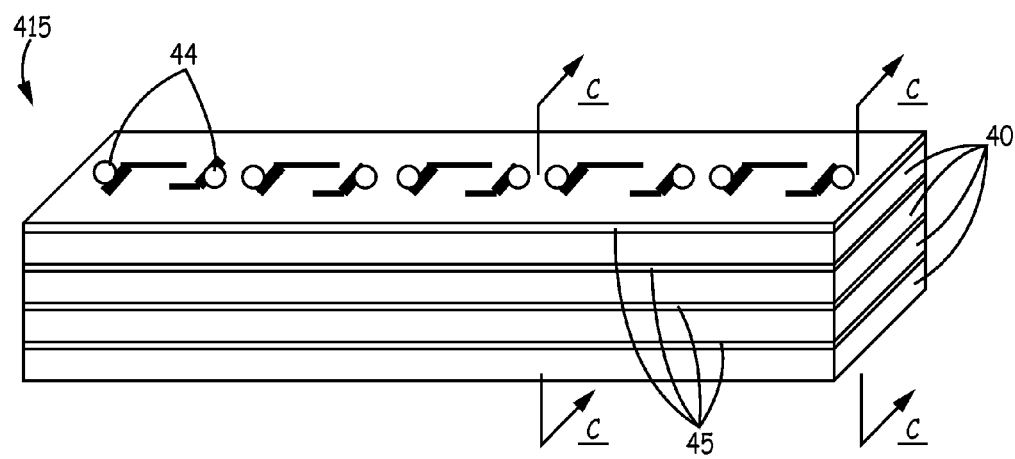
FIG. 4B is a perspective view of a plurality of the layers of FIG. 4A formed in a stack, according to some methods.

FIG. 4A is an exploded schematic of a single layer 405 of a stack 415 (FIG. 4B), fabricated according to some methods of the present invention; and FIG. 4B is a perspective view of stack 415 formed by a plurality of layers 405, according to some methods. FIG. 4A illustrates layer 405 including an array of the above-described planar solid state battery chips 32, which are contained in a wafer 40, which is known as an artificial or reconstituted wafer, formed by a polymer mold compound (i.e. an epoxy based thermoset including a non-conductive filler such as $AlO_2$ or $SiO_2$, about 80% by volume), in which battery chips 32 are embedded. FIGS. 4A-B further illustrate a redistribution layer (RDL) 45 formed over a surface of each wafer 40, wherein each RDL 45 includes a first group of conductive traces 451, each of which is coupled to a corresponding positive battery contact 301 (illustrated by dotted lines in FIG. 4A) and extends laterally therefrom, and a second group of conductive traces 452, each of which is coupled to a corresponding negative battery contact 302 (illustrated by dotted lines in FIG. 4A) and extends laterally therefrom. Those skilled in the art are familiar with redistributed chip packaging (RCP) processes employed to successively build up dielectric (i.e. epoxy or polyimide or benzocyclobutene polymer) films and corresponding conductive traces (i.e. copper) to create each RDL 45.

Figure 4C:
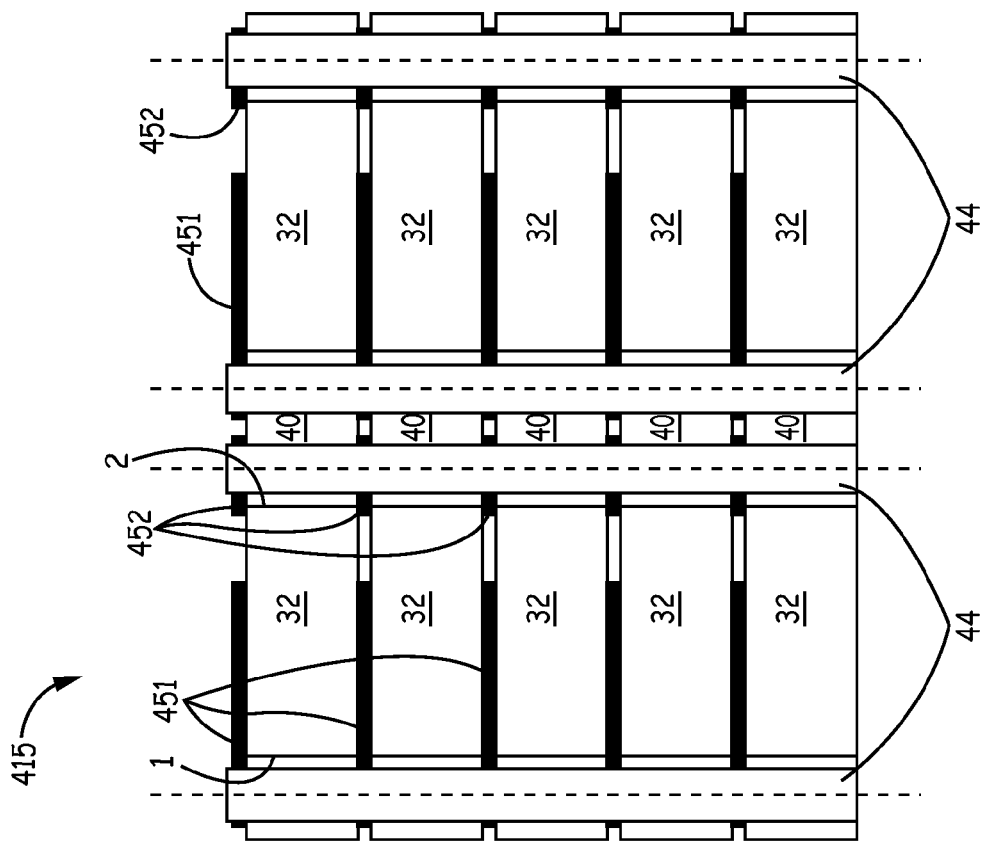
FIG. 4C is a cross-section view taken along a plane defined by section lines C-C of FIG. 4B.

According to the illustrated method/embodiment, each conductive trace 451 effectively extends the corresponding positive battery contact 301 just beyond a first edge 1 of a corresponding battery 32, and each conductive trace 452 effectively extends the corresponding negative battery contact 302 just beyond a second edge 2 of the corresponding battery 32. With reference to FIG. 4C, which is a cross-section view taken along a plane defined by section lines C-C of FIG. 4B, after an RDL 45 is formed over each of a plurality of wafers 40, wafers 40 are adhered to one another, for example, with an epoxy adhesive, to form stack 415, such that the battery arrays of each layer 405 overlay one another in an aligned arrangement. The aligned arrangement locates each battery 32 of one layer 405 over a corresponding battery 32 of each other layer 405 so that corresponding traces 451, 452 are aligned for the formation of conductive vias 44, for example, by drilling holes through the aligned traces of stacked layers 405, and then filling each hole with a conductive material, such as copper. FIG. 4C illustrates each via 44 extending through the polymer mold compound of each wafer 40, adjacent corresponding edges 1, 2 of overlaying aligned batteries 32, and through a corresponding column of aligned traces 451, 452, to electrically couple together each positive battery contact 301 of each group of overlaying aligned batteries 32, and to electrically couple together each negative battery contact 302 of each group of overlaying aligned batteries 32.

Figure 4D:
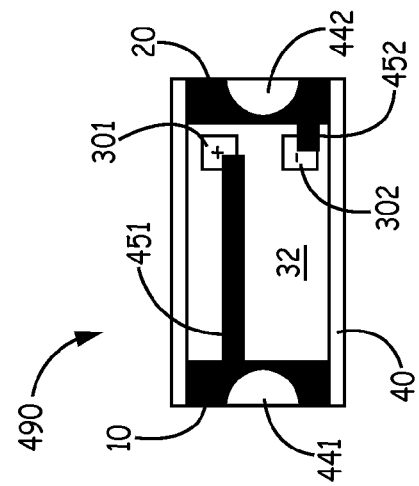
FIG. 4D is a top plan view of an individual battery stack singulated from the stack shown in FIGS. 4B-C, according to some embodiments.

The dashed lines in FIG. 4C represent cuts through stack 415, which are made following the formation of vias 44, to singulate individual battery stacks from stack 415. The illustrated cuts are located to dissect each via 44 so that each singulated battery stack, for example, like stack 490 shown in the top plan view of FIG. 4D, includes a first conductive channel 441 exposed along a first edge 10 of stack 490 and second conductive channel 442 exposed along a second edge 20 of stack 490. According to the illustrated embodiment, first channel 441 is electrically coupled to each positive battery contact 301 of stack 490, by corresponding conductive traces 451, and second channel 442 is coupled to each negative battery contact 302 of stack, by corresponding conductive traces 452, so that battery stack 490 can form a relatively high density power source in which channel 441 forms a positive terminal and channel 442 forms a negative terminal.

Figure 5A:
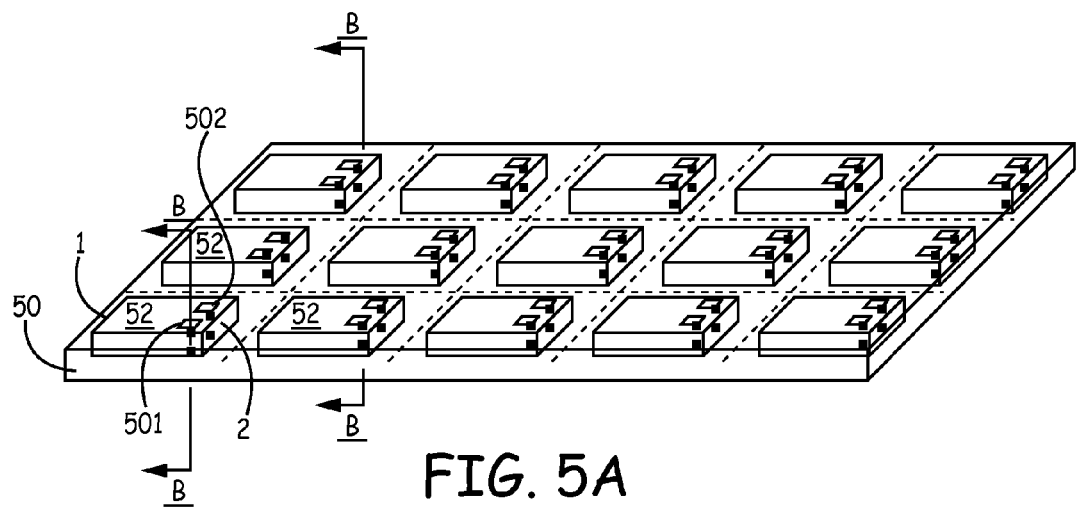
FIG. 5A is a perspective view of an exemplary wafer in which an array of planar solid state batteries is formed, according to an initial step of some alternate methods of the present invention.
Figure 5B:
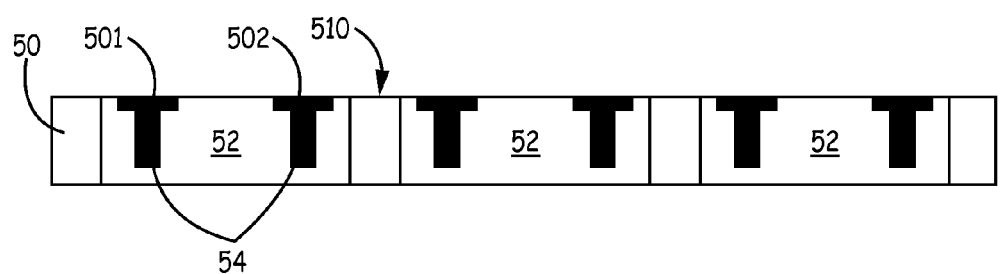
FIG. 5B is a cross-section view taken along a plane defined by section lines B-B of FIG. 5A.
Figure 5C:
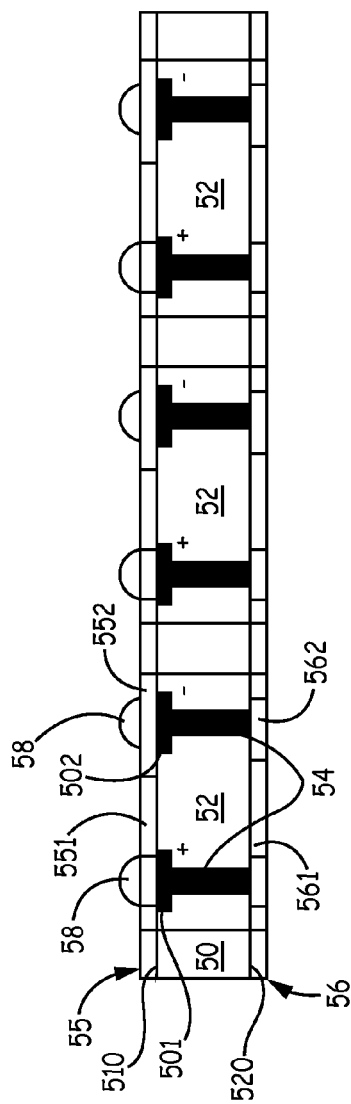
FIG. 5C is the same cross-section view as in FIG. 5B, but following several steps to form a single layer of a stack, according to the alternative fabrication methods.

With reference back to FIG. 4A, dashed lines represent optional recessed areas, which can be left when forming each RDL 45 in order to form a cavity between each adjacent battery 32 of each stack 490, according to some embodiments. The optional cavities can provide some stress and strain relief to individual battery stacks 490, if batteries 32 swell, during charge and discharge cycles. A height of each cavity preferably ranges between approximately one and five micrometers, which is sufficient for the aforementioned LiPON-type cell FIG. 5A is a perspective view of an exemplary wafer 50 in which an array of planar solid state batteries 52 is formed, according to an initial step of some alternate methods of the present invention; and FIG. 5B is a cross-section view taken along a plane defined by section lines B-B of FIG. 5A. According to the alternative methods, after some RCP processing, such as that described below, a plurality of wafers 50 are adhered together to form a stack 515 (FIG. 5D), wherein each wafer 50 is a silicon wafer in which batteries 52 are originally fabricated, for example, using thin-film cell construction techniques known in the art, and employing lithium phosphorous oxynitride (LiPON) electrolyte material. FIGS. 5A-B illustrate each battery 52 including a positive and negative contacts 501, 502 and blind vias 54, which are formed through each contact. After forming each via 54, by methods known to those skilled in the art, a first redistribution layer 55 is formed over a first side 510 of each wafer 50, for example, as illustrated in FIG. 5C; each first RDL 55 includes a plurality of first conductive traces 551, each of which is coupled to a corresponding positive battery contact 501 and extends laterally therefrom to a first edge 1 (FIG. 5A) of the corresponding battery 52, and a plurality of second conductive traces 552, each of which is coupled to a corresponding negative battery contact 502 and extends laterally therefrom to a second edge 2 of the corresponding battery 52. Following the formation of each first RDL 55, each wafer 50 is thinned, according to grinding or polishing methods known in the art, such that each via 54 extends to a second side 520 of the corresponding wafer 50, as shown in FIG. 5C. Following the thinning, a second redistribution layer 56, which includes a plurality of conductive bonding runners 561, 562 is formed over second side 520 of each wafer 50, wherein each runner 561, 562 corresponds to a trace 551, 552.

Figure 5D:
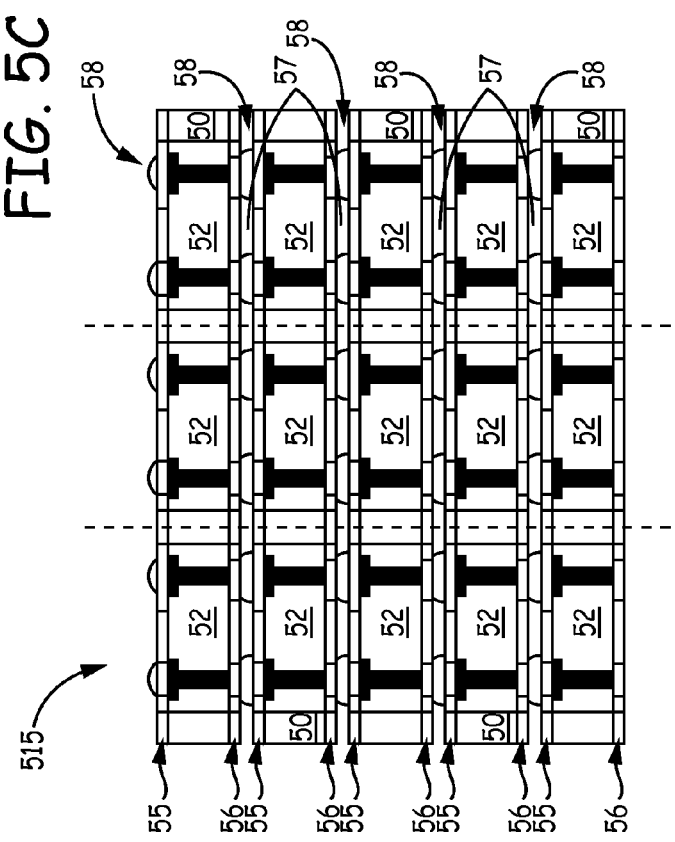
FIG. 5D is a similarly oriented cross-section view after a plurality of the layers of FIG. 5C are stacked, according to some methods.
Figure 5E:
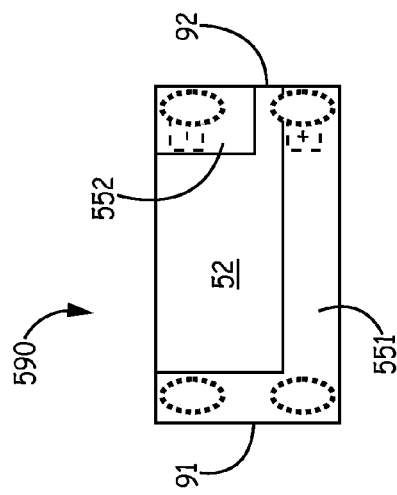
FIG. 5E is a top plan view, of an individual battery stack "singulated"/separated from the stack of wafers shown in FIG. 5D, according to some embodiments.

Next, with reference to FIGS. 5C and 5D, in order to adhere a plurality of wafers 50 together to form stack 515, a plurality of conductive bond pads 58, for example, formed from thin layers or micro-bumps of a solder compound, such as AuSn or SnPb, or formed from a conductive film epoxy adhesive, are applied to first RDL 55 for adhering to the bonding runners 561, 562 of the confronting second RDL 56 of the adjacent wafer 50 in stack 515, either by a reflow process, if solder, or by bonding, if adhesive. According to the illustrated embodiment, when stack 515 is formed, the array of batteries 52 contained in each wafer 50 overlay one another in a similar aligned arrangement as that described above for stack 415, and each bond pad 58 is located over a corresponding conductive trace 551, 552, for example, at each corner of each battery 52, as shown by the dotted outlines in FIG. 5E. After stack 515 is formed, cuts, for example according to the dashed lines shown in FIGS. 5A and 5D, are made to singulate/separate individual battery stacks from stack 515, for example, like stack 590 shown in the top plan view of FIG. 5E. According to the illustrated embodiment, each first conductive trace 551 extends to a first edge 91 of stack 590 and each second conductive trace 552 extends to a second edge 92 of stack 590; traces 551 and bonding runners 561 electrically connect together the corresponding vias 54 that extend through the aligned positive battery contacts 501 of each battery 52, and traces 552 and bonding runners 562 electrically connect together the corresponding vias 54 that extend through the aligned negative battery contacts 502 of each battery 52, such that battery stack 590 forms another embodiment of a relatively high density power source.

With further reference to FIG. 5D, when wafers 50 are adhered together in stack 515, conductive bond pads 56 preferably provide standoff to leave a cavity 57 between each adjacent and aligned battery 52. Cavities 57, like those described above, can have a height ranging between approximately one and five micrometers and can provide some stress and strain relief to individual battery stacks 590, if batteries 52 swell, during charge and discharge cycles.

In the foregoing detailed description, the invention has been described with reference to specific methods and embodiments. However, it may be appreciated that various modifications and changes can be made without departing from the scope of the invention as set forth in the appended claims.

The invention claimed is:

1. A power source for an implantable medical device, the power source comprising:
 a plurality of planar solid state batteries overlaying one another in an aligned arrangement and adhered to one another to form a stack, the stack having first and second edges extending along a height of the stack, the first and second edges being opposite one another;
 a first group of conductive vias, each via of the first group extending through a positive contact of a corresponding battery and approximately parallel to the first edge of the stack;
 a second group of conductive vias, each via of the second group extending through a negative contact of a corresponding battery and approximately parallel to the first edge of the stack;
 a first group of redistribution layers, each redistribution layer of the first group of redistribution layers extending over a first surface of a corresponding battery and each including a first conductive trace, coupled to the positive battery contact of the corresponding battery, and a second conductive trace, coupled to the negative contact of the corresponding battery, each first conductive trace extending to the first edge of the stack, and each second conductive trace extending to the second edge of the stack; and
 a second group of redistribution layers, each redistribution layer of the second group of redistribution layers extending over a second surface of a corresponding battery, the second surface opposite the first surface, and each second group of redistribution layers including a conductive bonding runner, each conductive bonding runner being coupled to a corresponding via of the first and second groups of conductive vias and to a corresponding conductive trace of an adjacent and confronting redistribution layer of the first group of redistribution layers.

2. The power source of claim 1, wherein the plurality of planar solid state batteries are adhered to one another by reflow of a solder compound against each conductive bonding runner, the solder compound being coupled to and located over each conductive trace and corresponding battery contact.

3. The power source of claim 1, wherein the plurality of planar solid state batteries are adhered to one another by bonding a conductive epoxy adhesive to each conductive bonding runner, the adhesive being coupled to and located over each conductive trace and corresponding battery contact.

4. The power source of claim 1, further comprising a cavity between adjacent batteries, each cavity having a height ranging between approximately one micrometers and approximately five micrometers.

* * * * *